United States Patent
Zhu et al.

(10) Patent No.: US 8,229,759 B2
(45) Date of Patent: Jul. 24, 2012

(54) SELF-SERVICE MEDICAL SERVICE METHOD AND ITS SYSTEM

(75) Inventors: Zhaofeng Zhu, Shanghai (CN); Qiang Gu, Shanghai (CN); Mingao Zhang, Shanghai (CN); Wanju Sun, Shanghai (CN); Zhonghua Du, Shanghai (CN); Like Zhao, Shanghai (CN)

(73) Assignee: Shanghai Pudong New Area People's Hospital, Shanghai (CN)

( * ) Notice: Subject to any disclaimer, the term of this patent is extended or adjusted under 35 U.S.C. 154(b) by 381 days.

(21) Appl. No.: 12/569,688

(22) Filed: Sep. 29, 2009

(65) Prior Publication Data

US 2011/0077969 A1    Mar. 31, 2011

(51) Int. Cl.
  *G06Q 10/00*    (2012.01)
  *G06Q 50/00*    (2012.01)
(52) U.S. Cl. .................................. 705/2; 705/3
(58) Field of Classification Search ............ 705/2–3
  See application file for complete search history.

(56) References Cited

U.S. PATENT DOCUMENTS

| | | | |
|---|---|---|---|
| 7,761,463 B2* | 7/2010 | Wheeler | 707/769 |
| 2004/0186744 A1* | 9/2004 | Lux | 705/2 |
| 2006/0111941 A1* | 5/2006 | Blom | 705/2 |

* cited by examiner

*Primary Examiner* — Luke Gilligan
*Assistant Examiner* — Joseph Burgess
(74) *Attorney, Agent, or Firm* — Squire Sanders (US) LLP

(57) ABSTRACT

The present invention provides a medical self-service terminal service method and system thereof. It is based on the integrated IHE information management system, radiology management system, digital image technology, computer technology, and tele-communication technology. It converts information and images of the patient and diagnosis information of doctors into digital computer information and stores them in a server. The patient information and medical image data can be called in, displayed, printed, and output via a network. Human-oriented animated interfaces and accurate and simple operation options help patients choose all kinds of self-services needed, such as registration, log-in, photograph pickup, report pickup, and querying, through human-computer interaction in different periods of time.

7 Claims, 6 Drawing Sheets

SELF-SERVICE MEDICAL SERVICE METHOD AND ITS SYSTEM

TECHNICAL FIELD

This invention relates to an information query/search system, in particular to a self-service medical terminal method based on Hospital Information System (HIS) and its system.

BACKGROUND

With the rapid development of computer and network technology, the all-round digitalization and networking of applied medical information has become an important task of construction of new-type digital hospitals. The comprehensive application of HIS (Hospital Information System), PACS (Picture Archiving & Communication System), RIS (Radiology Information System) and LIS (Laboratory Information System) has attracted attention from more and more professionals. However, the procedure of seeing a doctor involves registration, outpatient service, photographing or lab tests, photograph pickup or lab test reports, and payment, the lounges of current hospitals are often crowed with patients that wait in lines to register before the work hours of outpatient service and registration windows are often crowed with people that pick up reports during rush hours. By analyzing the present workflow of the medical process of hospitals we can see that: people need to wait in lines for registration, for taking or picking up photographs, and for picking up reports. Standing a line of the entire process takes a lot of time (usually 1-2 h). A patient has to spend much more time on queuing than on seeing a doctor. Many hospitals wish to solve these problems, and the development and improvement of the HIS functions have facilitated patients and ensured the timely clinical treatment.

SUMMARY

The purpose of this invention is to provide a medical self-service service method and system thereof. It is based on the integrated IHE information management system, radiology management system, digital image technology, computer technology, and tele-communication technology. It converts information and images of the patient and diagnosis information of doctors into digital computer information and stores them in a server. The patient information and medical image data can be called in, displayed, printed, and output via a network. Human-oriented animated interfaces and accurate and simple operation options help patients choose all kinds of self-services needed, such as registration, log-in, photograph pickup, report pickup, and querying, through human-computer interaction in different periods of time.

The medical self-service method provided by the present invention comprises the following steps:

Registration: based on dedicated registration software of the HIS system a charging and registration processing module dedicated to the medical self-service terminal service equipment is provided under the main menu of the software. It connects the patient information with the HIS database (Sybase) via the medical insurance card or return-visit card;

Doctor selection: the patient selects the department and doctor according to the doctor information (for example, doctors' resumes, specialties, successful cases, and availability status, etc.,) in the database. Once the patient completes the selection and pays charges according to the charge message, he will receive a registration charge note bearing visit number of the department and office. This information will be stored in the server and queued for the visit.

Visiting (seeing a doctor): after said doctor selection information is processed, when it is the visiting patient's turn, the information of this patient (visiting No., patient's name, doctor's name, and doctor's room No., etc.,) will be displayed synchronously with self-service registration. And then the patient starts to see the doctor.

Photographing or lab test analysis: if the doctor believes that the patient needs a X-ray or CT photographing or blood analysis, the doctor will select corresponding items in the system and register them by sending an auxiliary diagnosis request via an electronic request note.

The patient pays for said photographing or lab test analysis via a self-service payment terminal or a charge-collecting window.

Said photographing or lab test analysis information and patient's payment information is processed by the system and sent to the photographing or lab test department. The department processes the information (and after queuing the patient) sends invitation information for the patient to carry out photographing or lab test analysis. This information will be displayed on an integrated display device of the hospital, indicating that the patient may carry out photographing or lab test analysis at the corresponding location.

Said photographing or lab test analysis information of the patient enters the system and is then sent by the server to the terminal of the diagnostician. After receiving the relevant information of the patient, the diagnostician makes the diagnosis and sends it to the upper-level doctor for reviewing. The reviewed picture & text report is directly sent to the server. And the photographing or lab test analysis information of the patient is broadcasted on the display or broadcasting devices of the hospital.

The doctor views the photographing or lab test analysis information of the patient and provides the professional report via the terminal. The patient may print the diagnosis report via a self-service terminal.

The medical self-service system provided by this invention comprises:

A central processing unit (CPU);

A patient and hospital information database connected to said central processing unit, used to store basic information of patients that visit the hospital and all kinds of information about doctors and the hospital. All departments of the hospital can use patients' medical insurance cards and visit cards to query the patients' basic information in the Sybase Database. The patient can also use simple operations on the interface to obtain all kinds of information needed for registration;

A registration module connected to said central processing unit that connects the patient information with the patient and to hospital information database via the medical insurance card or return-visit card of the patient and musters relevant information;

A doctor selection module connected to said central processing unit through which the patient can access doctors' information (doctors' resumes, specialties, successful cases, and availability status) in the hospital information database and select the department and doctor needed. This module will display several available doctors that match the patient's requirements. The patient can view doctors' information and select the most suitable doctor to visit. Once the selection is completed the patient pay charges according to the charge message, he will receive a visit number, and this information will be stored to said database;

A photographing or lab test analysis module connected to said central processing unit, used to process the X-ray, CT, MR, and other photographing or blood analysis data modules for the patient;

A card reading device connected to said central processing unit; this card reading device can read the patient's information (visit or return-visit information) and input it into said central processing unit. This processing unit will compare the read information with the information in the patient and hospital information database and timely update the database;

An integrated information display device connected to said central processing unit; combined with said central processing unit, it can timely display the patient's visiting information and lab test analysis information and instruct the patient to see the doctor or take lab tests at relevant places. In addition, said photographing and lab test analysis information and the charge payment information of the patient will be processed by said central processing unit and then sent to the radiology or test department. After processing (queuing) the information, the department will send an invitation for the patient to take the photograph or lab test analysis and display this invitation on an integrated display device. The patient can go to the test department to take the photograph or lab test analysis upon seeing or hearing such information;

A printing device connected to said central processing unit; it is connected to said central processing unit and can be used to call in and print out the patient's lab test report, payment documents, and radiological or image diagnosis report; and A medical self-service terminal connected to said central processing unit and operated by the patient.

Since lab test and diagnosis reports is automatically read and printed, and doctors can automatically be selected, and seeing a doctor is automatically registered and the patients are charges, the self-service medial terminal method and its system provided by the present invention can effectively solve long-standing difficult problems of queuing in all procedures of medication (registration, photograph pickup, report pickup, etc.) and thus improve the overall medication efficiency of a hospital.

EMBODIMENTS

This invention will be further described with detailed figures as below so that the technical means, creative features, purposes, and effects of this invention can be easily understood.

Figure 1:
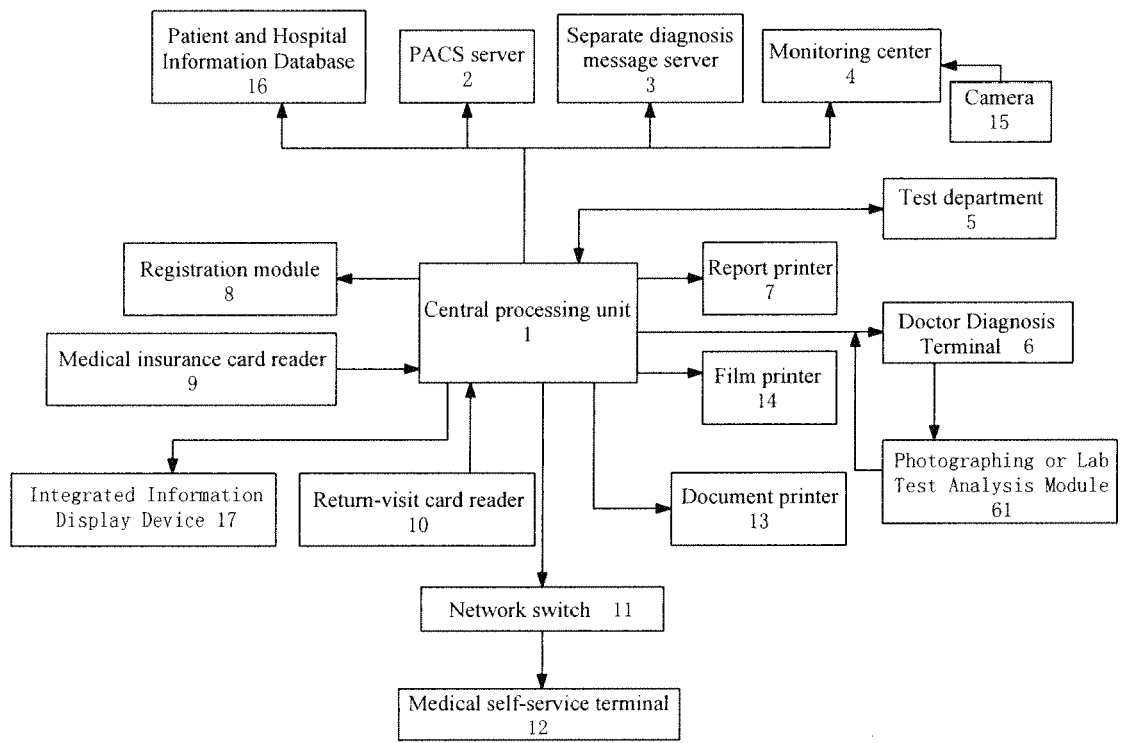
FIG. 1 is a schematic view of the structure of the self-service medical system provided by this invention.

As shown in FIG. 1, the medical self-service terminal service system provided by this invention comprises Central Processing Unit (CPU) 1, PACS Server 2, Separate Diagnosis Information Server 3, Monitoring Center 4, Registration Module 8, Medical Insurance Card Reader 9, Return-visit Card Reader 10, Report Printer 7, Film Printer 14, Document Printer 13, Test Department 5, Doctor Diagnosis Terminal 6, Network Exchanger 11, Patient and Hospital Information Database 16, Hospital Integrated Display Device 17, and Medical Self-service Terminal 12.

Central Processing Unit 1 is the management center of the entire service system of this invention and used to execute relevant programs.

Separate Diagnosis Information Server 3 is connected to said Central Processing Unit 1. It is used to collect the patient's relevant information and data information connected with medical insurance on a real-time basis. And it also provides the latest out-patient registration information of the hospital.

PACS Server 2 is connected to said Central Processing Unit 1. This PACS system (Picture Archiving & Communication System) is a combination of radiology, medical imaging, digital imaging technology, computer technology, and communication technology. It converts medical image data into digital computer information and performs the acquisition, display, storage, exchange, output and saving of medial image data.

Hospital Information Database 16 is connected to said Central Processing Unit 1. It is a database used to store the basic information of visiting patients and all kinds of doctors and hospital information. All departments of the hospital can use patients' medical insurance cards and visit cards to query the patients' basic information in the Sybase Database. The patient can also use simple operations on the interface to obtain all kinds of information needed for registration. The doctor can also obtain the hospital or patient information.

Integrated Information Display Device 17 is connected to said Central Processing Unit 1. It timely displays the visiting information and lab test analysis information of the patient and instructs the patient to visit the doctor or take the lab test at the relevant department. The information of patients that have gone through the registration procedure and entered the separate diagnosis system, the information of patients whose image diagnosis reports have been finished, and notification messages of patients whose test or other diagnosis reports have been completed are all transmitted to the LED screen in the hall via the Hospital Information System (HIS) and PACS Server 2.

Registration Module 8 is connected to said central processing unit 1. The patient uses the medical insurance card or return-visit card to connect to Patient and Hospital Information Database 16 via Central Processing Unit 1. Registration Module 8 contains a doctor selection module through which the patient can acquire doctors' information from said Patient and Hospital Information Database 16. This information includes doctors' resume, available departments, (such as the Gastroenterology Department, the Surgical Department, the Neurology Department, and the Cardiovascular Department), professional titles (such as Professor, Associate Professor, Doctor-in-charge, and Physician), successful cases, and availability status etc. When the patient inputs the name of the needed department or doctor, the central processing unit 1 will acquire a list of available doctors from said patient and hospital information database 16, such as information of two or more doctors and the department information and parameters needed for this visit. This module will display several available doctors that match the patient's requirements. The patient can view doctors' information and select the most suitable doctor to visit. Once the selection is completed and the patient pays the charges according to the charge message, finally he will receive a visit number, and this information will be stored to said database.

Doctor Diagnosis Terminal (doctor) 6 is connected to said Central Processing Unit 1. It contains a Photographing or Lab Test Analysis Module 61. If the doctor believes that the patient needs take X-ray, B-ultrasound, or other photographing or blood analysis, the X-ray, CT, or other photographing or blood analysis information will be transmitted to Central Processing Unit 1 via the module 61. Central Processing Unit 1 will process the data and then said photographing or lab test analysis information and the patient's charge payment information will be processed and sent to the Test Department 5. The department processes the information (and after queuing the patient) sends invitation information for the patient to carry out photographing or lab test analysis. This information will be displayed on Hospital Integrated Display Device 17, indicating that the patient may carry out photographing or lab test analysis at the corresponding location. The patient can go to Test Department 5 of the hospital to take the photograph or lab test analysis upon seeing such information.

This invention also has a card reading system comprising Medical Insurance Card Reader 9 and Return-visit Card Reader 10. This card reading system can read the patient's information (visit or return-visit information) and input it into said Central Processing Unit 1. Central Processing Unit 1 will compare the read information with the information in Patient and Hospital Information Database 16 and timely update the database. Dedicated equipment produced by manufacturers designated by the nation is used for the medical insurance card reader. The return-visit card reader is a crucial part of the entire equipment. All visiting patients at their own expenses have barcode return-visit cards. It is the input and output interface of the medical self-service system of this invention and an important part that ensures the accuracy and reliability of information read by the patient. The new-generation MS7625 embedded-type multi-line scanning device most recently provided by US company. METROLOGIC, can be used. Its most outstanding feature is the high sensitivity. This device offers high-speed and accurate scanning service and has all-direction and full-automatic card reading and scanning functions. The scanning speed is up to 2000 lines/s. Its excellent technical indexes can ensure the high reliability of the reading of patients' barcode information. And its external-connection DC and RS232 communication interfaces ensure the stability of the equipment.

This invention has a printing system comprising Report Printer 7, Film Printer 14, and Document Printer 13. This printing system is connected to said Central Processing Unit 1. it can be used to call in/search and print the patient's lab test reports, test photographs, and payment documents, etc. UP-D72XR digital thermal-sensitive film printer produced by Sony can be used as Film Printer 14, which is equipped with a standard DICOM3.0 interfaces and only needs about 65 seconds (65 s) to process and print a 8×10 film. When several frames of image films are printed, it only takes 40 s to print the second and the rest films. And clear and high-resolution images can be printed. An important reason for selecting this product is that it has overall dimensions as small as 42×210×43(cm). This feature can significantly reduce the dimensions of the entire equipment. And it consumes little power. The maximum power consumption during the printing process is only 286 W.

Medical Self-service Terminal 12 is an interface operating device connected to Central Processing Unit 1 through Network Exchanger 11. It is a terminal directly operated by the patient to handle/operate Registration Module 8, Medical Insurance Card Reader 9, Return-visit Card Reader 10, Report Printer 7, Film Printer 14, and Document Printer 13.

The medical self-service system of this invention also comprises a Monitoring Center 4. Monitoring Center 4 has a Camera 15 which is connected to Central Processing Unit 1 and used to monitor Medical Self-service Terminal 12. Once the patient performs any incorrect operation or needs help, the monitoring center will promptly notify the relevant person to provide the patient with advices.

Figure 2:
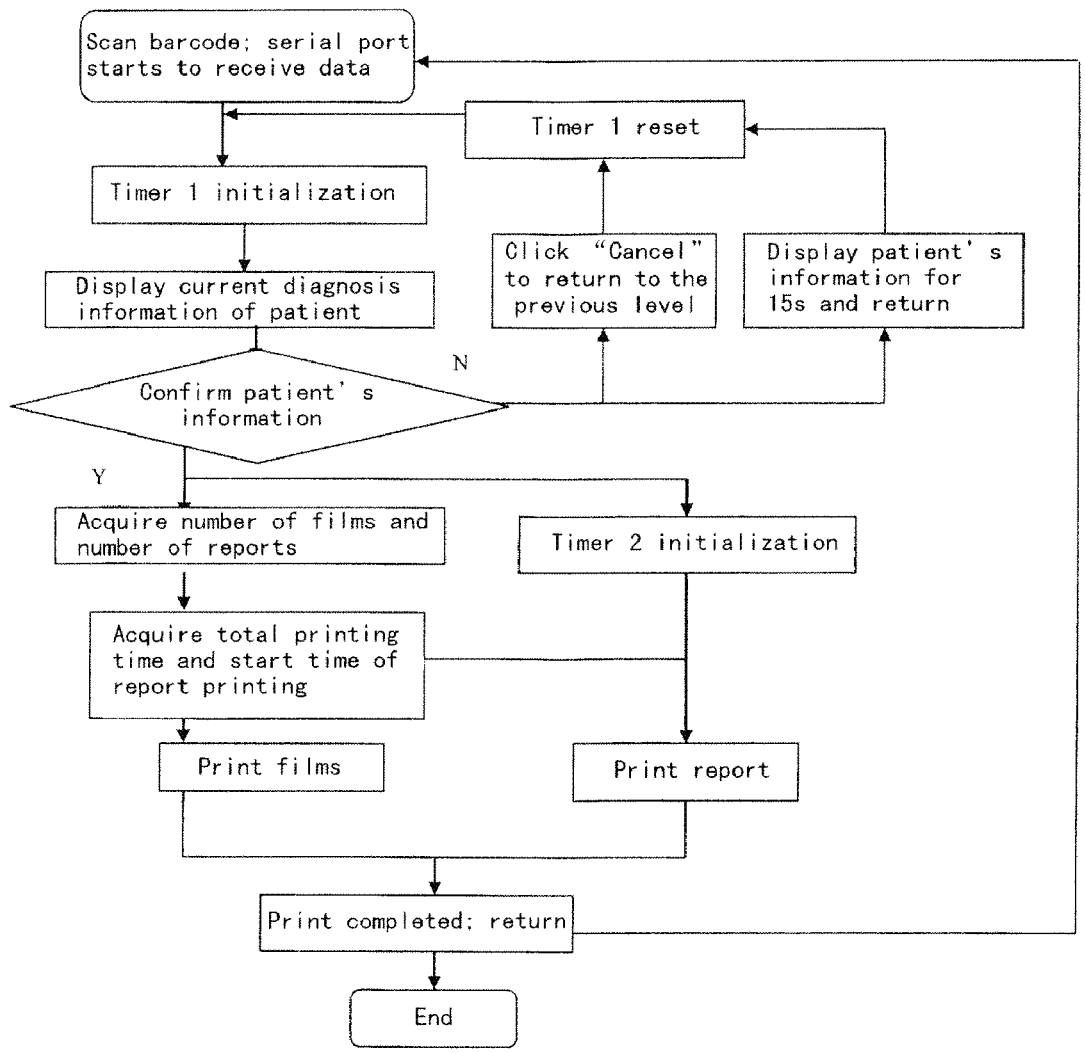
FIG. 2 is the flow chart of the automatic photograph pick-up process of the self-service medical system provided by this invention.

FIG. 2 is the flow chart of the process by which the patient prints test reports and photographs. After initialization the patient inputs his identification information (e.g. via Medical Insurance Card Reader 9 or Return-visit Card Reader 10 or directly by inputting information into Medical Self-service Terminal 12). If the information is correct the system will display the current diagnosis information of the patient. The patient then confirms the information that he needs to print and acquire the number of films of photographs and the number of diagnosis reports needed. Therefore the patient will spend some time on the printing system to acquire said films or diagnosis reports from its Report Printer 7, Film Printer 14, and Document Printer 13.

Figure 3:
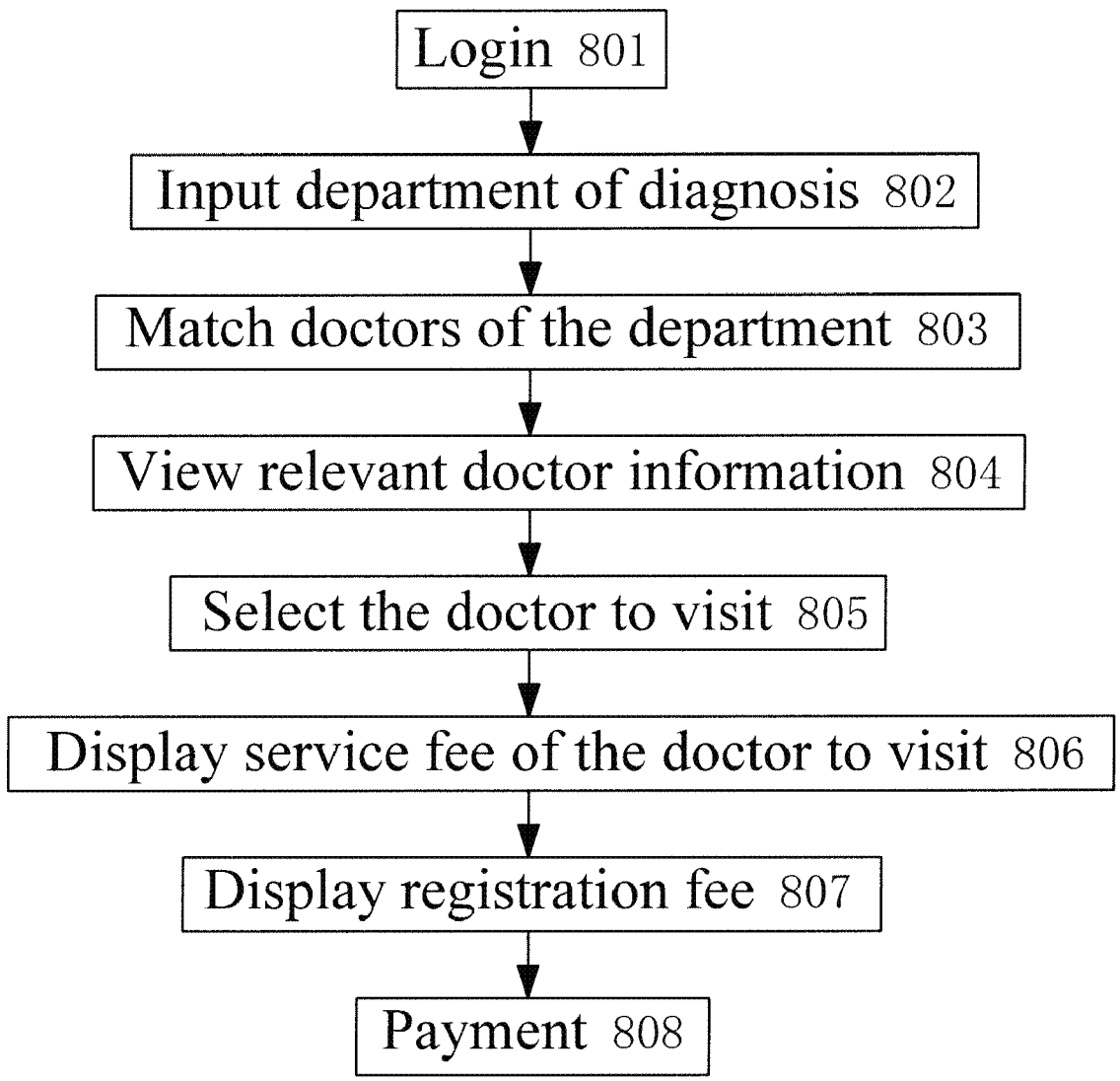
FIG. 3 is the flow chart of the registration process of the self-service medical system provided by this invention.

FIG. 3 is the flow chart of the process by which the patient registers with the registration system.

Step 801: the patient first performs registration via Medical Insurance Card Reader 9 or Return-visit Card Reader 10 or directly by inputting information into Medical Self-service Terminal 12.

Step 802: input the department to visit;

Step 803: search for doctors in the department;

Step 804: view and find out relevant information of doctors;

Step 805: select the suitable doctor to visit;

Step 806: the system displays the service fee of the doctor to be visited;

Step 807: the system displays registration fee;

Step 808: the patient pays the registration fee and doctor's service fee.

Figure 4:
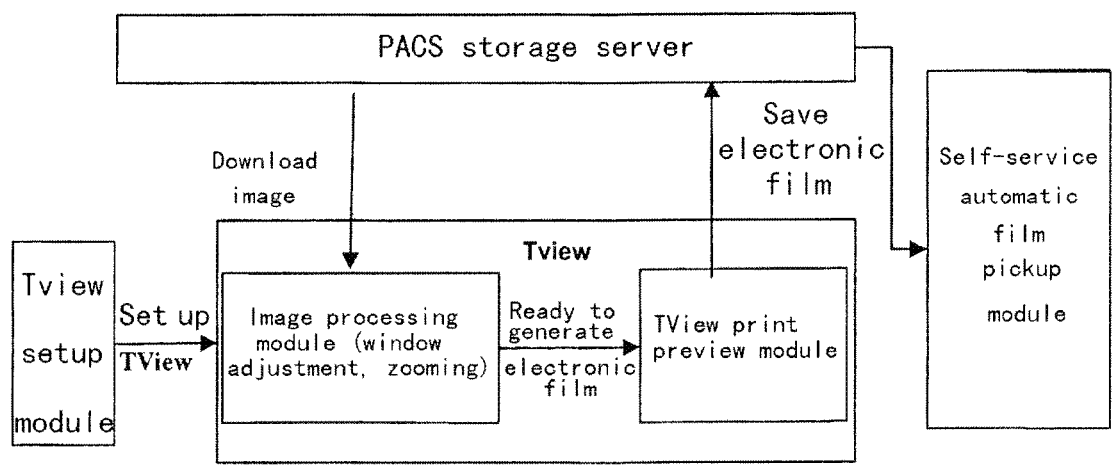
FIG. 4 is a block diagram of the workflow of PACS system for browsing, data acquiring, and generation of electronic films and processing of medical images.

FIG. 4 is a block diagram of the workflow of PACS system that browses, acquires, and generates electronic films and processes medical images. An electronic film processing module is designed for this equipment in the software. It is used to provide the patient's images source for the self-service automatic printers by connecting to SQL Server database, set up the Tview printer list, image download sources, and saving destinations and labels of electronic films through a "TView" module, and set up the saving destinations of electronic films (PACS). TView supports saving electronic films to any PACS that supports the DICOM3.0 standard. The reviewing doctor can properly process the patient's image with the window adjusting, zooming, cutting, rotating, and translating functions provided by TView and save the images in the form of electronic films, so that image films acquired by the patient from the medical self-service terminal have good display effects. After the report is reviewed, the patient's image whose window width and window position have been adjusted will be directly transmitted from the server to the DICOM film printer in the medical self-service terminal. After printing the film, the counter program will automatically add 1. And a function has been designed to stop repeated printing.

Figure 5:
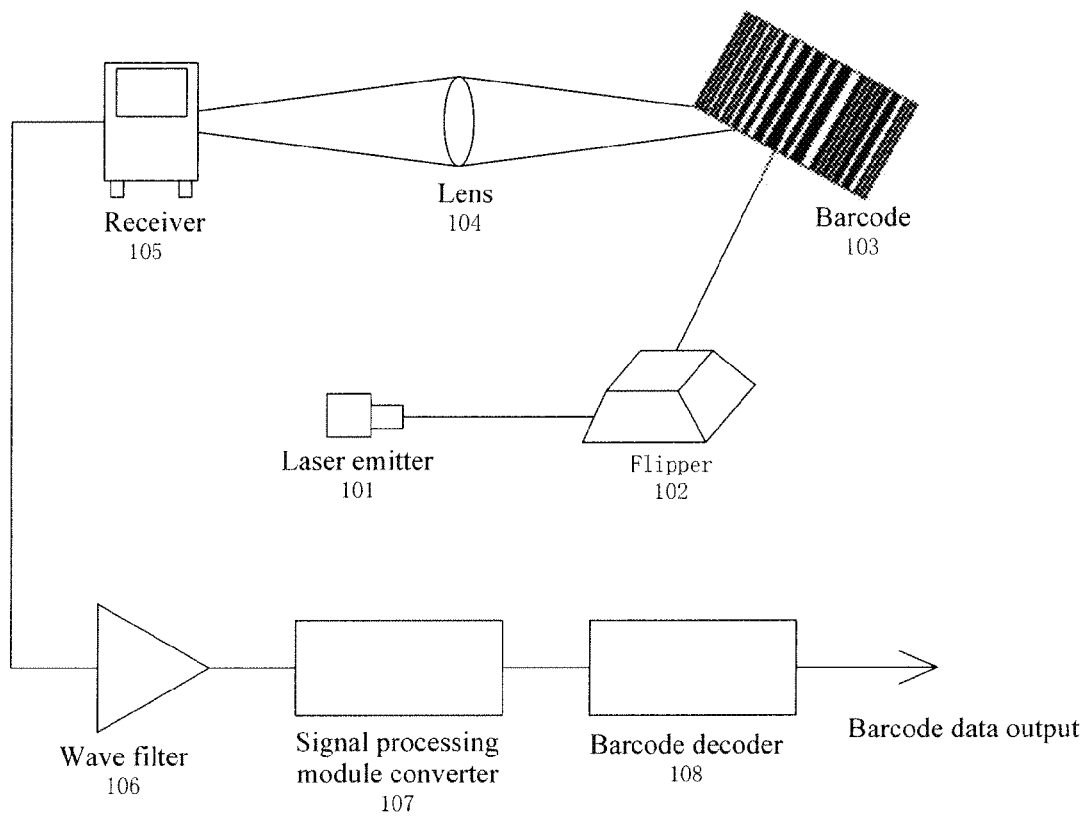
FIG. 5 is a schematic view of the structure of the card reading system for barcodes on patients' medical records provided by this invention.

FIG. 5 is a schematic diagram of the card reading system. Laser Emitter 101 scans Barcode 103 of the patient's medical record card through a Flipper 102. The scanned image is reflected to Receiver 105 by the way of Lens 104. The Receiver 105 sends the signal to Wave Filter 106 where its wave is filtered. Then it is converted by Signal Processing Module Converter 107 and input into Barcode Decoder 108 for decoding, after which the data information of the barcode is finally output.

Figure 6:
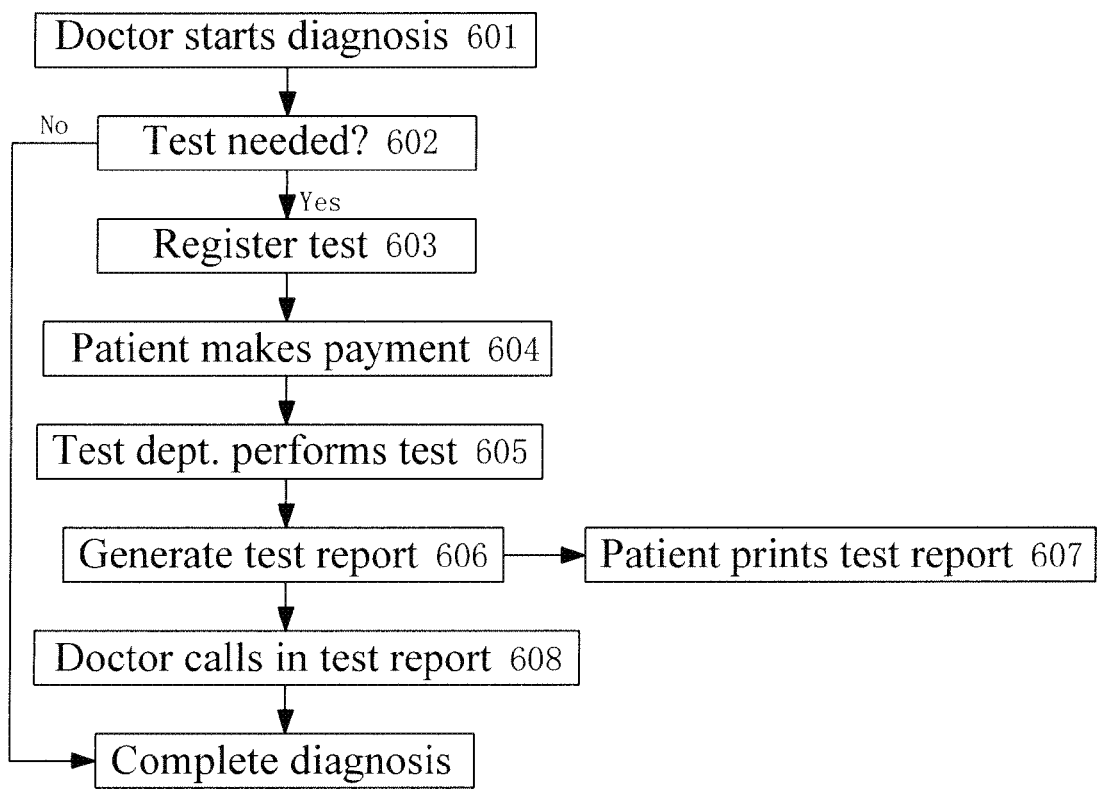
FIG. 6 is the flow chart of detecting or testing involved in doctor's diagnosis.

FIG. 6 is the flow chart of tests involved in the doctor's diagnosis.

Step 601: the doctor diagnoses the patient;

Step 602: the doctor decides if the patient needs any test;

Step 603: if the patient does need a test, the doctor registers the test at Doctor's Diagnosis Terminal 6 and input the test information into Central Processing Unit 1. Central Processing Unit 1 processes the information and sends it to Test Department 5.

Step 604: the patient pays the test fee;

Step 605: Test Department 5 conducts the test of the patient according to the test instructions;

Step 606: Test Department 5 completes the test and generates a test report;

Step 607: the patient prints test report by using Report Printer 7, Film Printer 14, and Document Printer 13 of the printing system.

Step 608: the doctor calls in the test report from PACS Server 2 via Central Processing Unit 1 and continues to diagnose the patient.

The basic principles and main features of this invention and the advantages of this utility model have been presented and described above. It must be understood by those with ordinary skill in the art that the embodiments illustrated above have been set forth only for the purposes of examples and that they should not be taken as limiting the invention. This invention is subject to all kinds of variations and improvements without departing from the essences and scope of this utility model. All these variations and improvements are contemplated as being equivalently within the scope of the claims. The scope of protection of this invention is defined by the attached Patent Claim and its equivalents.

What is claimed is:

1. A medical self-service method, comprising following steps:
    providing a charging and registration processing module dedicated to a medical self-service terminal service equipment under the main menu of a dedicated registration software of a hospital information system (HIS), wherein the equipment connects the patient information with the HIS database via a medical insurance card or a return-visit card;
    the patient selecting a department and a doctor that matches the patient's requirements according to the doctor information in the database, wherein the doctor information includes: doctors' resumes, specialties, successful cases, and availability status; and
    the patient paying charges according to the charge message and receiving a registration charge note bearing a visit number of the department;
    wherein the doctor selection information is stored in the server and queued for the visit;
    the patient visiting the doctor after the doctor selection information is processed, wherein the patient's information is displayed synchronously with self-service registration, wherein the patient's information includes visiting number, patient's name, doctor's name, and doctor's room number;
    the doctor selecting diagnostic items in the system and registering them by sending an auxiliary diagnosis request via an electronic request note for a photographing or a lab test;
    the patient paying for the photographing or lab test analysis via a self-service payment terminal or a charge-collecting window;
    the system processing the photographing or lab test analysis information and the payment information and sending the information to the photographing or lab test department;
    the photographing or lab test department processing the information and, after queuing the patient and, sending an invitation to the patient for photographing or lab test analysis,
    wherein the invitation is displayed on an integrated display device of the hospital, indicating that the patient may carry out photographing or lab test analysis at a designated location;
    the server of the system entering the photographing or lab test analysis information into the system and sending the same to the terminal of a diagnostician; then the diagnostician making a diagnosis after receiving the relevant information of the patient and then sending the diagnosis to an upper-level doctor for reviewing;
    the reviewed diagnosis being sent to the server directly and the photographing or lab test information of the patient is broadcasted on the display or broadcasting devices of the hospital;
    the doctor viewing the photographing or lab test analysis information and providing a diagnosis report via the self-service terminal;
    the patient printing the diagnosis report.

2. The medical self-service method according to claim 1, wherein
    in the registration step, the patient either performs registration via a medical insurance card reader or a return-visit card reader or directly inputs relevant information into the medical self-service terminal;
    in the doctor selection step, the patient inputs the department to visit, searches for doctors in the department, views relevant information of doctors; and selects a suitable doctor to visit; the system displays the service fee of the doctor to be visited and the registration fee; and the patient pays the registration fee and doctor's service fee.

3. The medical self-service method according to claim 1, wherein the doctor registers the patients lab test through the following steps:
    the doctor registering the test at a doctor's diagnosis terminal and inputting the test information into the central processing unit which processes the information and sends it to test department;
    the patient paying the test fee;
    the test department conducting the test according to the test instructions;
    the test department completing the test and generates a test report;
    the patient printing the test report by using the printing system; and
    the doctor calling in the test report from a picture archiving & communication system (PACS) server via the central processing unit and continuing to diagnose the patient.

4. The medical self-service method according to claim 1, wherein the patient prints the test report through the following steps:
    the patient inputting his identification information, the system displaying the current diagnosis information of the patient,
    the patient confirming the information that needs to be printed and acquiring the number of films or photographs and the number of diagnosis reports needed, the patient acquiring the films or diagnosis reports from the report printing system.

5. A medical self-service system, comprising:

a module configured for a patient processing self-service registration, wherein the module is dedicated to a medical self-service terminal equipment under the main menu of a dedicated registration software of a hospital information system (HIS), wherein the equipment connects the patient information with the HIS database via a medical insurance card or a return-visit card, a module configured for the patient selecting a department and a doctor that matches the patient's requirements according to the doctor information in the database, wherein the doctor information includes: doctors' resumes, specialties, successful cases, and availability status, wherein the doctor selection information is stored in the server and queued for the visit, a module configured for the patient paying charges according to the charge message and receiving a registration charge note bearing a visit number of the department, a module configured for displaying the patient's information synchronously with the self-service registration, wherein the patient's information includes visiting number, patient's name, doctor's name, and doctor's room number, a module configured for a doctor selecting diagnostic items in the system and registering them by sending an auxiliary diagnosis request via an electronic request note for a photographing or a lab test, a module configured for processing the photographing or lab test information and sending the information to a photographing or lab test department;

a module configured for the photographing or lab test department sending an invitation to the patient for photographing or lab test, a module configured for displaying the invitation to patient for photographing or lab test at a designated location, a module configured for entering the photographing or lab test analysis information into the system and sending the same to the terminal of a diagnostician for a diagnosis, a module configured for sending the diagnosis to an upper-level doctor for reviewing, a module configured for sending the reviewed diagnosis to the server of the system, a module configured for displaying the photographing or lab test analysis information of the patient, a module configured for the doctor viewing the photographing or lab test analysis information and providing a diagnosis report via the self-service terminal, and a module configured for printing the diagnosis report.

6. The medical self-service system according to claim 5, wherein the module displays several available doctors that match the patient's requirements.

7. The medical self-service system according to claim 5, wherein the photographing is selected from the group consisting of X-ray, CT, and MR.

* * * * *